US006544250B1

(12) United States Patent
Schaffer

(10) Patent No.: US 6,544,250 B1
(45) Date of Patent: Apr. 8, 2003

(54) BLIND CLINICAL TRIAL DEVICE

(75) Inventor: Peter Schaffer, Radolfzell (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 09/830,427

(22) PCT Filed: Nov. 5, 1999

(86) PCT No.: PCT/EP99/08476

§ 371 (c)(1), (2), (4) Date: Apr. 26, 2001

(87) PCT Pub. No.: WO00/27448

PCT Pub. Date: May 18, 2000

(30) Foreign Application Priority Data

Nov. 6, 1998 (DE) ........................................ 198 51 119

(51) Int. Cl.$^7$ .............................................. A61M 25/00

(52) U.S. Cl. ...................... 604/523; 604/403; 604/257; 206/438

(58) Field of Search ................................ 604/403, 407, 604/408, 32, 412, 232, 257, 523; 206/438, 69, 811; 220/592.01

(56) References Cited

U.S. PATENT DOCUMENTS 3,572,340 A * 3/1971 Lloyd et al. ................ 128/278
3,958,080 A * 5/1976 Schadler .................... 178/7.91
4,767,415 A * 8/1988 Duffy ......................... 604/232
5,376,081 A * 12/1994 Sapienza .................... 604/207
5,457,492 A * 10/1995 Sakaki et al. ............... 348/126
5,658,248 A * 8/1997 Klein et al. ................... 604/32
5,858,015 A * 1/1999 Fini ........................... 604/403
5,980,834 A * 11/1999 Bruno ........................ 422/102
6,287,284 B1 * 9/2001 Warbuton-Pitt ............. 604/257
2002/0094506 A1 * 7/2002 Fischer et al. ................ 433/90

FOREIGN PATENT DOCUMENTS

DE 255260 A3 3/1988
WO WO 97/05914 2/1997

* cited by examiner

*Primary Examiner*—Ira S. Lazarus
*Assistant Examiner*—Tu Cam Nguyen
(74) *Attorney, Agent, or Firm*—Gary M. Nath; Todd L. Juneau; Sheldon M. McGee

(57) ABSTRACT

The present invention relates to a device for blinding the administration of nonsolid pharmaceutical presentations. The device is in particular an opaque container which has at least two attachments, one of which is intended for connection to a dispenser for the pharmaceutical presentation, and the other of which is intended for connection to an applicator, the inside of said container having means for holding back the pharmaceutical presentation.

20 Claims, 3 Drawing Sheets

BLIND CLINICAL TRIAL DEVICE

TECHNICAL FIELD OF THE INVENTION

The invention relates to a device for blinding the administration of nonsolid pharmaceutical presentations in clinical trials on mammals.

PRIOR ART

In the prior art there are various known ways of blinding the administration of nonsolid presentations in clinical trials. If the pharmaceutical presentation is a colorless liquid, then the pharmaceutical presentation can be replaced for example by a physiological saline solution. In the case of colored presentations, an opaque application system, for example, can be used for administration. It is obvious that these methods are not suitable for intrapulmonary administration. In the case of clinical testing of nonsolid presentations which are administered by the intrapulmonary route, the double-blind technique is therefore used. [J. A. Schwarz (1995), Leitfaden Klinische Prüfungen: Planung, Organisation, Durchführung, Dokumentation und Überwachung (Guidelines for Clinical Trials: Planning, Organization, Conduct, Documentation and Monitoring), ECV-Editio Cantor-Verlag; Der pharmazeutische Betrieb; Vol. 43; or M. S. Kwong et al., Double-Blind Clinical Trial of Calf Lung Surfactant Extract for the Prevention of Hyaline Membrane Disease in Extremely Premature Infants; Pediatrics (1985), Vol. 76, No. 4, pages 585–592]. Here, the test substance is administered by persons who are not otherwise involved with the patient during the clinical study. These persons are then under a pledge of secrecy. The double-blind technique can only be carried out with considerable outlay in terms of personnel and costs.

SUBJECT OF THE INVENTION

It is an object of the present invention to make available a device for blinding the administration of nonsolid pharmaceutical presentations in clinical trials in a simple manner and without using the double-blind technique.

The subject of the invention is therefore a device for blinding the administration of nonsolid pharmaceutical presentations in clinical trials on mammals.

In one aspect of the invention, the device is an opaque container which has at least two attachments, one of which is intended for connection to.a dispenser for the pharmaceutical presentation, and the other of which is intended for connection to an applicator, and where the inside of the container has means for holding back the pharmaceutical presentation (hereinafter also referred to as the nonflow-type configuration).

When such a container is connected to a dispenser and to an opaque applicator for administration of a pharmaceutical presentation, said pharmaceutical presentation is held back in the container upon application, but this cannot be detected by the person charged with the administration.

In a further aspect, the invention concerns an opaque container which has at least two attachments, one of which is intended for connection to a dispenser for the pharmaceutical presentation, and the other of which is intended for connection to an applicator, and where the attachments in the inside of the container have a continuous connection which ensures that the pharmaceutical presentation is transported through the container (hereinafter also referred to as the flow-type configuration).

If this container is used together with a dispenser and an opaque applicator to administer the pharmaceutical presentation, said pharmaceutical presentation is transported through the container and administered to the patient, but this cannot be detected by the person charged with the administration.

In a further aspect, the invention relates to a container with which it is possible both to transport the pharmaceutical presentation through the container and also to hold back the pharmaceutical presentation in the same container. A further subject of the invention is therefore an opaque container which has at least three attachments, two of which are intended for connection to a dispenser for the pharmaceutical presentation, and the third one of which is intended for connection to an applicator, and where the inside of the container has means for holding back the pharmaceutical presentation, and one of the attachments which are intended for connection to a dispenser has a continuous connection to the attachment which is intended for connection to the applicator, and the connection ensures that the pharmaceutical presentation is transported through the container.

Depending on the choice of attachments for connection to the dispenser and the applicator, the pharmaceutical presentation is either transported through the container and administered to the patient or is held back in the container.

The container according to the invention can be rigid or flexible and can be made from all suitable solid materials. The container is advantageously one which has been made using plastic or rubber (e.g. film bag made of PVC film).

The means for holding back the pharmaceutical presentation inside the container is preferably an absorbent material which is not able to completely take up the nonsolid pharmaceutical presentation (e.g. absorbent fabric). However, the container can also be completely or partially hollow on its inside. The pharmaceutical presentation can also be held back in this way. Depending on the nature of the means for holding back the pharmaceutical presentation (hereinafter also referred to as the test substance), the container is preferably dimensioned such that it can completely accommodate the test substance to be administered. In a preferred embodiment of the invention, the container is dimensioned such that it can accommodate 300 ml of liquid. Containers are preferred which have an internal volume of 500 ml to 3000 ml, and particularly preferred are those which have an internal volume of 1000 ml to 2000 ml.

Depending on the weight and the quantity of the test substance to be administered, the container should preferably have a correspondingly greater own weight. This makes it difficult or even impossible for the person administering the substance to compare the weight of the container before and after administration of the test substance. Containers with an own weight of more than 1 kg have generally proven advantageous in this respect. In a preferred embodiment of the invention, the inside of the container can have weight elements in order to ensure an adequate own weight of the container. The weight elements can for example be hard rubber disks.

The attachments which the container according to the invention possesses are preferably commercially available Luer lock attachments which are suitable for connection to the dispenser and applicator. The attachments preferably have different markings for purposes of differentiation. The dispenser is preferably a commercially available syringe which can be connected to the attachment on the container directly or via a tube connection. The applicator is preferably an opaque applicator, for example an opaque catheter system, preferably a catheter system which is suitable for intrapulmonary administration of a nonsolid pharmaceutical presentation. Such catheters are known to those versed in the art.

The container according to the invention which holds back the pharmaceutical presentation can, at the attachment intended for connection to the dispenser, also be connected to a tube which leads into the inside of the container and has an open end through which the pharmaceutical presentation is dispensed into the inside of the container. The tube advantageously has a plurality of openings in the tube line. This ensures rapid dispensing of the pharmaceutical presentation into the inside of the container. The tube can also advantageously have a nonreturn valve which ensures that the pharmaceutical presentation dispensed into the inside of the container cannot return into the tube. The attachment intended for connection to the applicator can have a closure inside the container, so that the pharmaceutical presentation held back cannot escape into the applicator. If so desired, this can entail a closed tube guided through the inside of the container. In a preferred embodiment of the invention, the two tubes leading into the inside of the container can be connected to one another via a Y-connector. The tube which leads to the attachment for the applicator is tied off sealingly or is tightly sealed by means of pinching or welding. The 3rd attachment of the Y-connector has an open cap through which the delivered pharmaceutical presentation can flow into the blinding bag.

The container according to the invention which ensures transport of the pharmaceutical presentation through the container advantageously has, inside the container, a continuous tube connection between the attachments. The container can be hollow or, if so desired, can also be filled with suitable materials, for example absorbent materials, and weight elements. The container is preferably designed corresponding to the container which holds back the pharmaceutical presentation in the container.

The container according to the invention can also have a venting device (e.g. valve) in order to compensate for pressure differences which arise thorugh the pharmaceutical preparation being held back in the container.

The containers according to the invention are suitable, together with a dispenser and an applicator, for advantageously blinding the administration of nonsolid presentations, in particular liquid presentations, by the intrapulmonary route. Examples of liquid presentations are pharmaceutical presentations which have the properties of natural lung surfactant. Reference is made by way of example to the presentations described in WO95/32992.

If, during a clinical trial, containers with and containers without retention of the pharmaceutcial presentation are used by the same person, the various containers are preferably designed in such a way that a distinction cannot be made between them by said person.

Illustrative embodiments of the invention are explained in more detail below with reference to the drawings, in which.

Figure 1:
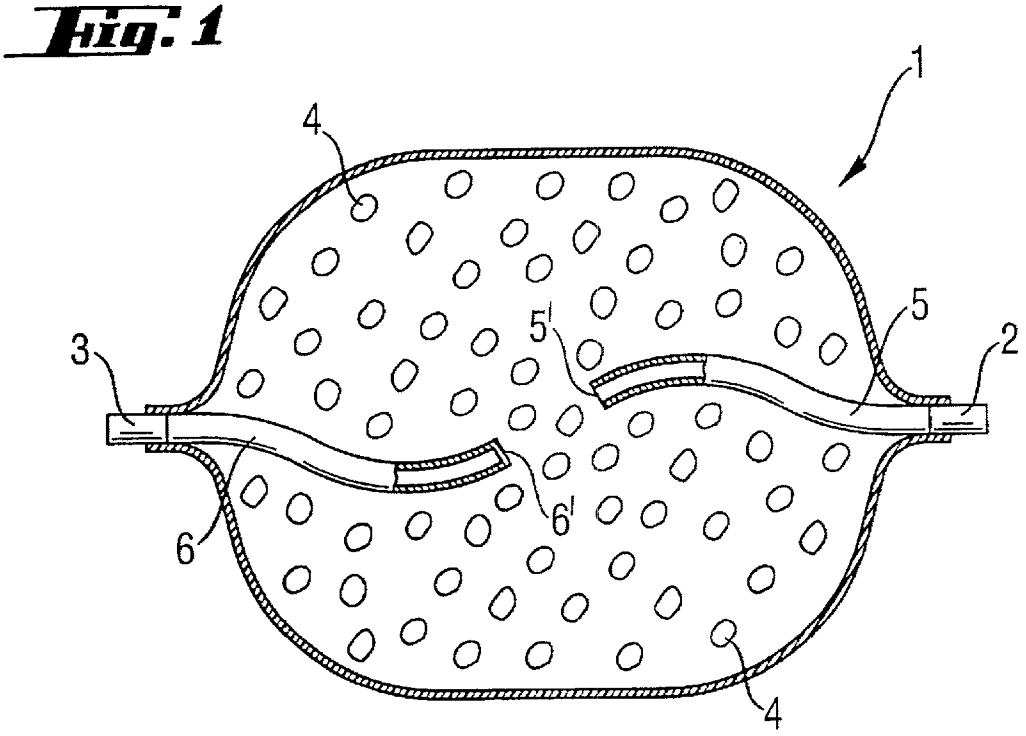
FIG. 1 is a diagrammatic cross section of one embodiment of an opaque container which holds back the pharmaceutical presentation in the container.

FIG. 1 shows the embodiment, according to the invention, of a container 1 which has an attachment 2 intended for connection to a dispenser and an attachment 3 intended for connection to an applicator. The container 1 is filled with an absorbent material 4. The container 1 has, at the attachment 2, a tube 5 which leads into the inside of the container 1 and which is open at its end 5'. The attachment 3 likewise has a tube 6 which leads into the inside of the container and which is closed at its end 6'.

Figure 2:
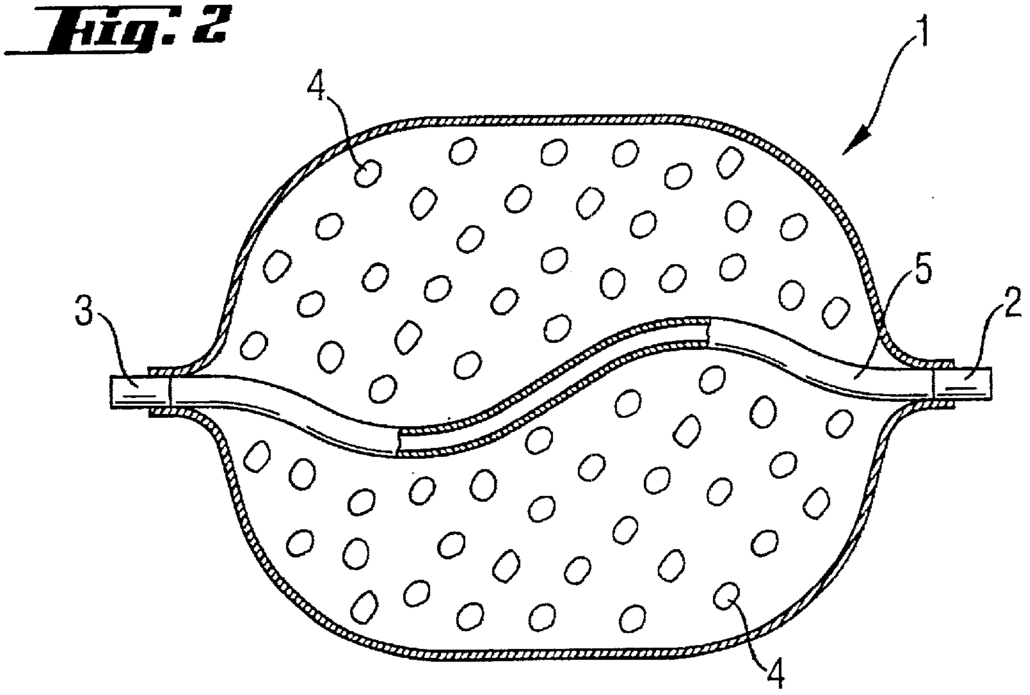
FIG. 2 is a diagrammatic cross section of an embodiment, according to the invention, of an opaque container which ensures that the test substance is transported through the container.

FIG. 2 shows the embodiment, according to the invention, of a container 1 which has an attachment 2 intended for connection to a dispenser and an attachment 3 intended for connection to an applicator. The attachments 2 and 3 are connected inside the container 1 via a continuous tube 5. The container 1 is filled with an absorbent material 4.

Figure 3:
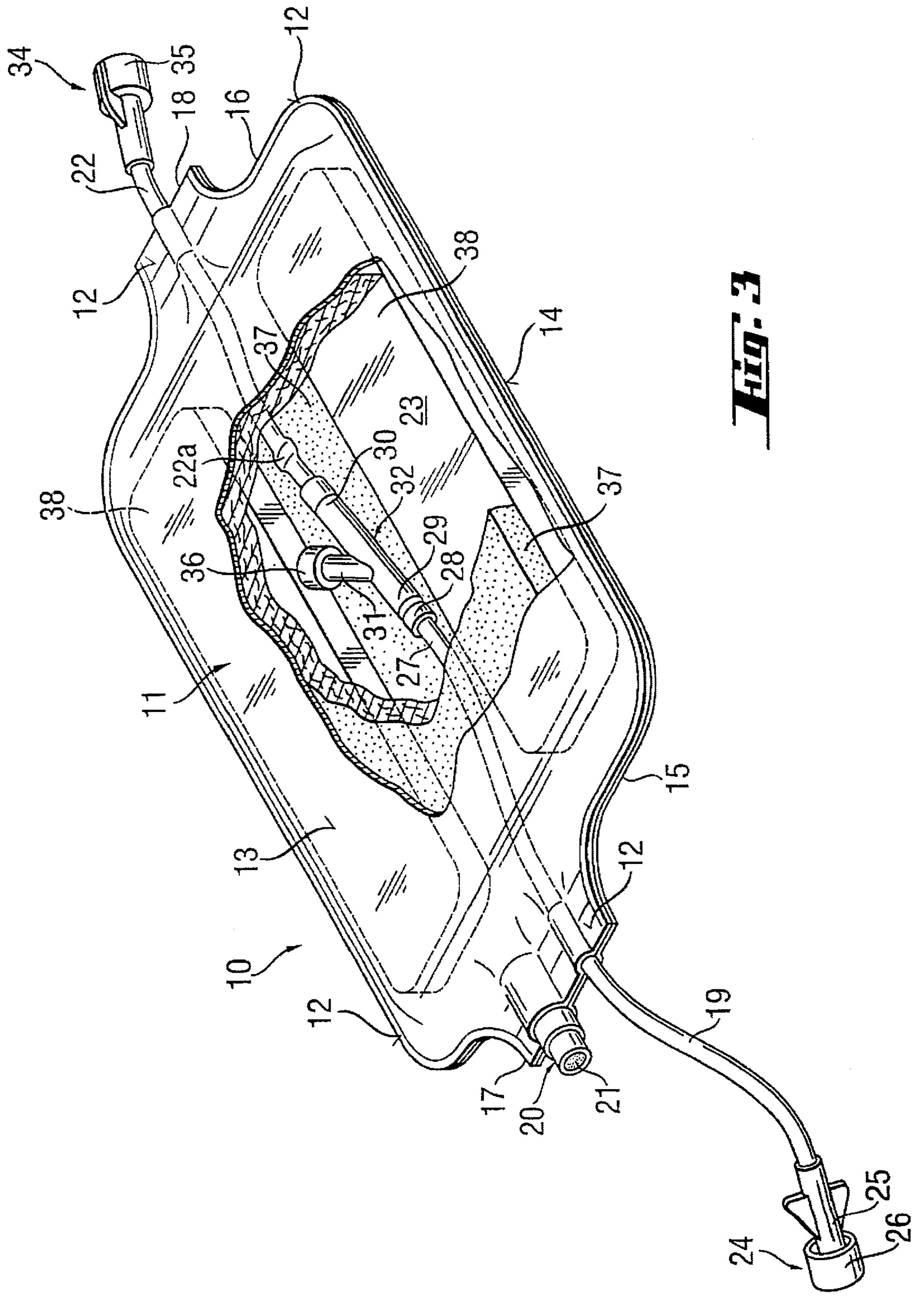
FIG. 3 shows a container according to the invention (hereinafter also referred to as blinding bag) in a nonflow-type configuration, in a partially cut-away perspective view.

A blinding bag 10 according to the invention, represented by way of example in FIG. 3 in the nonflow-type configuration, has a film bag 11 formed by two preferably opaque film blanks 13, 14 which are connected to one another sealingly along their edges by means of welding or adhesive 12. At its opposite narrow ends 15, 16, the film bag 11 has neck-like projections 17, 18 into which on the one hand a tube 19 is introduced for conducting a medium (e.g. test substance) and a venting device 20, and, on the other hand, an outlet tube 22. The venting device 20 is equipped with a conventional filter 21 for microbe-free removal of air from the inside 23 of the blinding bag 10. At its free outer end 24, the inlet tube 19 has a so-called Luer lock attachment element 25 of female configuration, which has a cap-like adapter 26. That end 27 of the inlet tube 19 inside the bag is provided with a nonreturn valve 28 which prevents medium from flowing back into the inlet tube 19. The nonreturn valve 28 is connected to a 1st attachment 29 of a Y-connector 32, which with its 2nd attachment 30 is connected sealingly to the outlet tube 22. At its outer end 34, the outlet tube 22 has a so-called Luer lock attachment element 35 of male configuration, which can be connected to a tube system which is connected for example to a patient (not shown). The outlet tube 22 is tied off sealingly inside the blinding bag 10 or sealed by means of pinching or welding 22*a*. In the inside 23 of the film bag 11 or blinding bag 10 there are one or more layers of an absorbent material 37 which is able to take up and bind a defined quantity, for example, of a medium. Provided at the 3rd attachment 31 of the Y-connector 32 there is an open cap 36 through which the medium fed via the inlet tube 19 can flow into the inside 23 of the blinding bag 10 and can be taken up by the absorbent structure 37. Moreover, two weighting elements 38 are advantageously provided in the inside of the blinding bag 10 to conceal an increase in weight.

Figure 4:
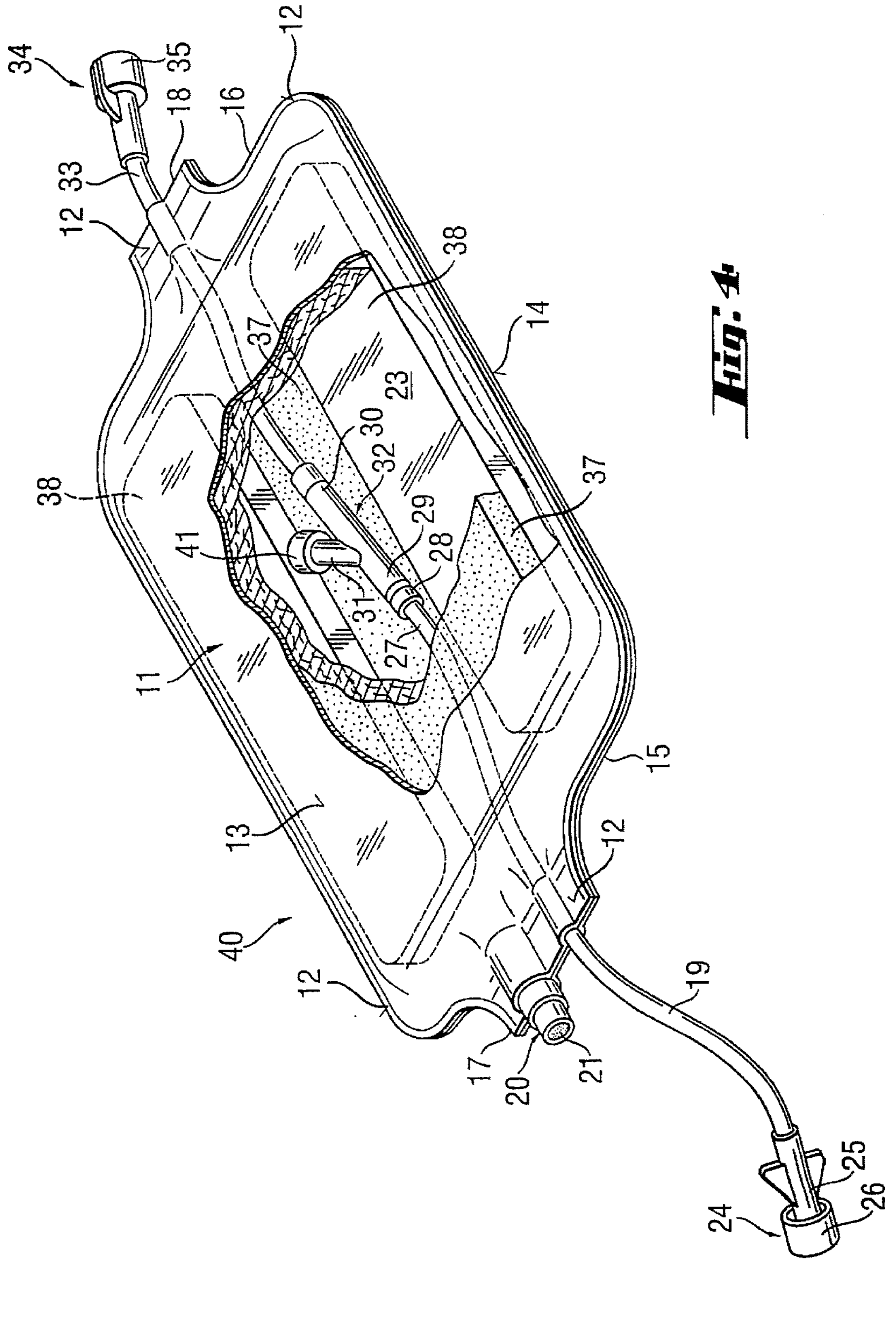
FIG. 4 shows a blinding bag according to the invention in a flow-type configuration, in a representation according to FIG. 3.

A blinding bag 40 according to the invention, shown according to FIG. 4 in the flow-type configuration, basically has the same elements as the nonflow-type configuration according to FIG. 3, which is indicated here by the same references. In contrast to FIG. 3, the outlet tube 33 is in this case designed open, so that a medium can flow through the blinding bag 40. Provided at the 3rd attachment 31 of the Y-connector 32 there is a closed cap 41, i.e. no medium can flow into the inside 23 of the blinding bag.

What is claimed is:

1. An opaque container (1) for blinding the administration of nonsolid pharmaceutical presentations in clinical trials on mammals, which has at least two attachments, (2, 3), one of which is intended for connection to a dispenser for the pharmaceutical presentation, and the other of which is intended for connection to an applicator, the inside of said container (1) having means (4) for holding back the pharmaceutical presentation, wherein the attachment intended for connection to the applicator has a closure inside the container.

2. An opaque container (1) for blinding the administration of nonsolid pharmaceutical presentations in clinical trials on mammals, which has at least two attachments (2,3), one of which is intended for connection to a dispenser for the pharmaceutical presentation, and the other of which is intended for connection to an applicator, the attachments in the inside of the container having a continuous connection (5) ensuring that the pharmaceutical presentation is transported through the container (1).

3. An opaque container (1) for blinding the administration of nonsolid pharmaceutical presentations in clinical trials on mammals, which has at least three attachments (2,2,3), two of which are intended for connection to a dispenser for the pharmaceutical presentation, and the third one of which is intended for connection to an applicator, the inside of said container (1) having means (4) for holding back the pharmaceutical presentation, and one of the attachments (2) which are intended for connection to a dispenser has a continuous connection (5) to the attachment (3) which is intended for connection to the applicator, and the connection ensures that the pharmaceutical presentation is transported through the container (1).

4. A device for blinding the administration of nonsolid pharmaceutical presentations in clinical trials on mammals, comprising a container (1) as claimed in claim 1.

5. The device as claimed in claim 4, characterized in that the device moreover has a syringe and a catheter system intended for pulmonary administration.

6. The container (1) as claimed in claim 1, characterized in that the container (1) has an absorbent material inside it.

7. The container (1) as claimed in claim 1, characterized in that attachments (2, 3) are Luer lock attachments.

8. The container (1) as claimed in claim 1, characterized in that the container (1) is made of rubber or plastic.

9. The container as claimed in claim 1, characterized in that inside the container an inlet tube (19) connected to a nonreturn valve (28) is connected to a $1^{st}$ attachment (29) of a Y-connector (32), which with its $2^{nd}$ attachment (30) is sealingly connected to an outlet tube (22), and the outlet tube (22) is sealed inside the container, and at the 3rd attachment (31) of the Y-connector (32) there is an open cap (36) through which the pharmaceutical presentation can flow into the inside of the container.

10. The container as claimed in claim 2, characterized in that inside the container an inlet tube (19) connected to a nonreturn valve (28) is connected to a $1^{st}$ attachment (29) of a Y-connector (32), which with its $2^{nd}$ attachment (30) is sealingly connected to an outlet tube (33), and at the $3^{rd}$ attachment (31) of the Y-connector (32) there is a sealed cap (41), and the outlet tube (33) is of open design.

11. A device for blinding the administration of nonsolid pharmaceutical presentations in clinical trials on mammals, comprising a container (1) as claimed in claim 2.

12. A device for blinding the administration of nonsolid pharmaceutical presentations in clinical trials on mammals, comprising a container (1) as claimed in claim 3.

13. The device as claimed in claim 11, characterized in that the device moreover has a syringe and a catheter system intended for pulmonary administration.

14. The device as claimed in claim 12, characterized in that the device moreover has a syringe and a catheter system intended for pulmonary administration.

15. The container (1) as claimed in claim 2, characterized in that the container (1) has an absorbent material inside it.

16. The container (1) as claimed in claim 3, characterized in that the container (1) has an absorbent material inside it.

17. The container (1) as claimed in claim 2, characterized in that attachments (2, 3) are Luer lock attachments.

18. The container (1) as claimed in claim 3, characterized in that attachments (2, 3) are Luer lock attachments.

19. The container (1) as claimed in claim 2, characterized in that the container (1) is made of rubber or plastic.

20. The container (1) as claimed in claim 3, characterized in that the container (1) is made of rubber or plastic.

* * * * *